United States Patent [19]
Rittenburg

[11] Patent Number: 5,710,005
[45] Date of Patent: Jan. 20, 1998

[54] ANALYTE DETECTION WITH A GRADIENT LATERAL FLOW DEVICE

[75] Inventor: James H. Rittenburg, Perkasie, Pa.

[73] Assignee: Biocode, Inc., Cambridge, Mass.

[21] Appl. No.: 741,855

[22] Filed: Oct. 29, 1996

[51] Int. Cl.[6] .................................................. C12Q 1/68
[52] U.S. Cl. ................... 435/6; 422/56; 422/58; 422/61; 435/5; 435/7.22; 435/7.31; 435/7.32; 435/7.4; 435/7.93; 435/7.94; 435/970; 435/975; 436/501; 436/512; 436/514; 436/169; 436/807; 436/808; 436/816; 436/817; 436/901
[58] Field of Search ........................ 422/56, 58, 61; 435/5, 6, 7.22, 7.31, 7.32, 7.4, 7.93, 7.94, 970, 975; 436/501, 512, 514, 164, 169, 807, 808, 810, 816, 817, 824, 827, 828, 901

[56] References Cited

U.S. PATENT DOCUMENTS

| | | |
|---|---|---|
| 3,983,005 | 9/1976 | Goodhue et al. . |
| 4,069,017 | 1/1978 | Wu et al. . |
| 4,144,306 | 3/1979 | Figueras . |
| 4,366,241 | 12/1982 | Tom et al. . |
| 4,968,604 | 11/1990 | Beatty ............................ 422/56 X |
| 5,354,692 | 10/1994 | Yang et al. . |
| 5,356,785 | 10/1994 | McMahon et al. . |
| 5,527,686 | 6/1996 | Fitzpatrick et al. . |
| 5,620,901 | 4/1997 | Kauvar ............................ 422/56 |

FOREIGN PATENT DOCUMENTS

| | | |
|---|---|---|
| WO95/16207 | 6/1995 | WIPO . |
| WO95/16208 | 6/1995 | WIPO . |

*Primary Examiner*—Susan Wolski
*Attorney, Agent, or Firm*—Clark & Elbing LLP

[57] ABSTRACT

Methods for determining the concentration of an analyte in a sample in which an analyte gradient is established and brought into contact with one or more zones that contain binding members that interact with the analyte and thereby produce a detectable signal. Devices that may be used to practice the disclosed methods are also provided.

37 Claims, 12 Drawing Sheets

ANALYTE DETECTION WITH A GRADIENT LATERAL FLOW DEVICE

BACKGROUND OF THE INVENTION

The invention relates to analyte detection.

Lateral flow devices (LFDs) can be used outside the confines of a clinical or laboratory setting to detect the presence of various analytes in biological or other samples. Generally, these devices are simple, disposable, and self-contained. A common feature of LFDs is an absorbent sample application pad that draws the sample laterally, by capillary action, across one or more reagents that interact with the analyte (if it is present in the sample) and produce a measurable signal. The principle underlying LFDs is the same as that underlying other detection methods such as RIAs (radioimmunoassays) and ELISAs (enzyme-linked immunosorbant assays): the reagents in the LFD must specifically bind or otherwise interact with the analyte being tested.

Examples of absorptive-pad assay devices and methods are described in U.S. Pat. Nos. 3,983,005, 4,069,017, 4,144,306, 4,366,241, and 5,354,692.

SUMMARY OF THE INVENTION

The invention features methods and devices for determining the concentration of an analyte in a sample by establishing an analyte concentration gradient and bringing that gradient into operable contact with one or more zones within a novel lateral flow device. These zones include, as described below, an indicator zone, a test zone, and a control zone. Devices that can be used to perform each of the methods described herein are also features of the invention.

In one embodiment, the concentration of an analyte in a sample is determined by establishing an analyte gradient, bringing that gradient into operable contact with an indicator zone that contains a mobile binding member, and then bringing the indicator zone into operable contact with a test zone that contains a fixed binding member.

In a second embodiment, the concentration of an analyte in a sample is determined by establishing an analyte gradient and bringing that gradient into operable contact with a test zone that contains a fixed binding member.

In a third embodiment, the concentration of an analyte in a sample is determined by establishing an analyte gradient, bringing that gradient into operable contact with a test zone containing a fixed binding member, and then bringing an indicator zone that contains a mobile binding member, into operable contact with the test zone.

In each embodiment, a detectable signal, which indicates the concentration of the analyte in the sample, is produced in the test zone.

The methods and devices described herein can be used in the context of basic scientific research, the practice of medicine, including veterinary and dental medicine, forensic analysis, environmental protection studies, industrial or chemical manufacturing, and the development and testing of pharmaceutical, food, and cosmetic products.

The analyte detected may be, for example, a biological substance such as a hormone, an enzyme, an immunoglobulin, a bacterial, viral, parasitic, or fungal antigen, or the like. Alternatively, the analyte may be a drug that is administered in the course of treating a disease or a drug of abuse such as a barbiturate, an amphetamine, methadone, morphine, cocaine, codeine, dilaudid, tetrahydrocannabinol, or diazepam. Other detectable analytes include those generated by the manufacture of food, industrial agents, or chemical products. Examples of such analytes include food additives (e.g. bulking agents, vitamins, colorants or flavorants), agrichemicals (such as pesticides, insecticides, herbicides, and fertilizers), surfactants (e.g., sodium dodecylsulfate), adhesives (e.g. isocyanate glues), resins (e.g. wood resins and epoxy resins), organic pollutants (e.g. dioxins), and process chemicals (e.g. chemicals used in water systems) such as flocculating polymers, biocides, corrosion inhibitors, and anti-scalants. In addition, the analyte can be a substance that is used for the purpose of marking or tracing a product or process.

Any liquid suspected of containing a specific analyte can be used as a sample. These liquids include physiological fluids such as whole blood, plasma, serum, urine, cerebrospinal fluid, ascites fluid, sweat, lymph, or other body fluids. The antigens or antibodies present in these fluids may be monitored in order to determine the severity of an infection or to gauge the progress of treatment. For example, tumor antigens shed into the bloodstream may be monitored following chemotherapy or radiation therapy.

Liquids obtained from manufacturing processes as well as liquids collected from the environment may also be analyzed by the invention described herein. For example, rainwater, or water from an ocean, river, lake, pond, or stream may be collected and analyzed.

The sample may be processed, if necessary, prior to analysis. For example, the sample may be centrifuged or filtered to remove particulate matter or buffered in order to allow more efficient detection of the analyte. Suitable buffers include any of those known to skilled artisans, such as a 1–1,000 mM solution of Tris (TRIZMA, Sigma Chemical Co., St. Louis, Mo.) or 1–1,000 mM TRIS (2-Amino-2-(hydroxy-methyl)-1, 3-propanediol). Other buffers include phosphate buffered saline (PBS), citrate buffer, or bicarbonate buffer.

Preferably, the methods and devices described herein will be used to detect $0.001-1\times10^7$ µg/l, more preferably, $0.1-1\times10^5$ µg/l, and most preferably $1-1\times10^4$ µg/l of analyte.

The invention may also be used to detect analytes that are initially contained within solid-phase samples. These analytes would simply be extracted and suspended or dissolved in liquid prior to analysis. The extraction process could be as simple as shaking a solid sample in a buffer such as those listed above, which could then be applied to the gradient lateral flow device. Solid samples may include biological tissues (obtained, for example, in the process of performing a biopsy), soil, or foliage.

The analyte gradient may be established in numerous ways. For example, the sample can be applied to a wedge-shaped sample application pad, the diluent can be applied to a wedge-shaped diluent application pad, with the gradient being established by bringing the sample and diluent application pads into contact with one another. These pads may consist of an absorbent material, examples of which are given below. Although it is expected that the analyte gradient will be established with sample- and diluent application pads or chambers that are both wedge-shaped, a gradient may be established by applying either the sample to a wedge-shaped pad and the diluent to a square or rectangular-shaped pad, and vice-versa. The sample- and diluent application pads or chambers can be designed to create a linear or non-linear analyte concentration gradient.

The edges of the sample and diluent application pads may be smooth, or one or more of their edges may be stepped, as stairs are stepped. The horizontal and vertical aspects of each step may be the same length, or one aspect may be longer than the other. Similarly, all of the steps may be identical, or they may differ. For example, the steps at the periphery of the gradient may be larger than the steps in the center of the gradient.

Alternatively, the analyte gradient may be produced by applying the sample to a wedge-shaped sample application chamber, applying a diluent to a wedge-shaped diluent application chamber, and bringing the contents of these two chambers into contact with one another. The chambers may be constructed from any material that is capable of forming and retaining a shape. Examples of such materials include plastics, plexiglass, and glass. The chambers may be shaped to create either a smooth or a stepped analyte gradient, as described above. To establish a stepped gradient, the sample-containing chamber and/or the diluent-containing chamber may be subdivided into a parallel array of wells that end squarely where the sample- and diluent-containing chambers are brought into contact with one another. The wells could be manufactured, for example, by adjoining a series of capillaries of varying height.

The analyte gradient will move, as further described below, into contact with either a mobile binding member in the indicator zone or a fixed binding member in the test zone. For example, in the first embodiment, the analyte gradient contacts the indicator zone, wherein the analyte associates with a mobile binding member. Subsequently, the mobile binding member, or the analyte associated therewith, comes into contact with the test zone and associates with a fixed binding member therein. Alternatively, the mobile binding member may be associated with an analogue of the analyte that has a different, preferably lower, binding affinity for the mobile binding member than does the analyte. In this instance, the analyte would displace the analogue, which may subsequently associate with the fixed binding member in the test zone. In the second embodiment, the analyte gradient contacts the test zone directly and associates with a fixed binding member therein. In the third embodiment, the analyte gradient first contacts the test zone and associates with a fixed binding member therein. Subsequently, the indicator zone is brought into contact with the test zone and a mobile binding member (from the indicator zone) associates with either the fixed binding member in the test zone or the analyte associated therewith.

The binding member in the indicator zone is mobile (i.e., able to move out of that zone), whereas the binding member in the test zone is fixed (i.e., unable to move out of that zone). Otherwise, the binding members are equivalent and may include any substance that is capable of binding to, or otherwise specifically interacting with, either the analyte or another binding member that is associated with the analyte. Examples of binding members include antibodies, or a fragments thereof, antigens, haptens, biotin, avidin, lectins, carbohydrates, nucleic acid molecules, cells, or fragments thereof, enzymes, Protein A, molecularly-imprinted polymers, or receptors, such as those naturally present on the surfaces of cells.

In addition, either the fixed binding member or the mobile binding member may be associated with a signalling substance. Examples of signalling substances include colored particles such as colloidal metals (e.g., colloidal gold), carbon, silica, and latex; enzymes such as horseradish peroxidase and alkaline phosphatase; fluorophores such as fluorescein and rhodamine; liposomes; chemiluminescors; and chromophores. As indicated by the preceding list of examples, the signalling substance may be a visible substance, such as a colored latex bead, or it may participate in a reaction by which a colored product is produced. The reaction product may be visible when viewed with the naked eye, or may be apparent, for example, when exposed to a specialized light source, such as ultraviolet light. Although it is expected that viewing the test zone (either directly or indirectly) will be the primary way in which the test result is obtained, other methods, for example where the analyte is associated with a radioactive substance that is detected by subsequent exposure to X-ray film, are also considered within the scope of the invention.

The concentration of analyte in the sample, which interacts with the binding member, will be indicated by how much of the binding member, or the signalling substance, subsequently becomes associated with the test zone. A reaction within the test zone, that produces a measurable reaction product, indicates the analyte concentration.

Also featured in the invention are devices for determining the concentration of an analyte in a sample. These devices consist of a defined sample application region, a defined diluent application region, and a test zone. At least one of the sample- and diluent application regions will have a varying width, and they will be arranged so that they may be brought into contact with each other. A detectable signal that indicates the concentration of the analyte is produced in the test zone.

By "wedge-shaped" is meant any shape, which can be drawn by joining three or more lines, one end of which is an acute-angled edge formed by two converging planes. The wedge-shaped pad or wedge-shaped chamber used in the invention will taper from a relatively large edge, or "base", to a relatively small edge, or "tip". Typically, the tip of the sample application pad or chamber will be adjacent to the base of the diluent application pad or chamber, and vice-versa. When arranged in this way the diluent pad or chamber is said to be "complementary" to the sample pad or chamber. The sample and diluent application pads or chambers may or may not be identical in size or in every dimension. Furthermore, either the sample application pad, the diluent application pad, or both, may have either smooth edges or contours or one or more stepped edges or contours.

The sample application pad or chamber and the diluent application pad or chamber may be separated by any space or physical barrier that effectively prevents contact between the sample and diluent, and that, when dislocated, allows an analyte gradient to be established. An example of such a physical barrier is a strip of hydrophobic polystyrene. Alternative means of bringing the sample into operable contact with the diluent are described and illustrated below.

Optionally, the devices of the invention may include an indicator zone that may be positioned either between the analyte gradient and the test zone (i.e., downstream of the sample and diluent application pads or chambers and upstream of the test zone) or downstream of the all of these elements (i.e., downstream of the sample application pad or chamber, the diluent application pad or chamber, and the test zone). In the later instance, the device may be called, as illustrated in Example 3, a gradient reverse LFD.

Optionally, the devices of the invention may include a control zone, wherein a detectable signal that is independent of the analyte is produced. Thus, the control zone may serve as an indication that the device is functioning properly. For example, the control zone may contain a substance that specifically binds or otherwise specifically interacts with the binding member or the signalling substance that moves downstream from the indicator zone. Typically, the control zone will be positioned in the vicinity of the test zone.

Optionally, the devices of the invention may include one or more absorbent pads that are positioned to facilitate the lateral flow of the analyte gradient through the indicator zone, the test zone, or the control zone.

Optionally, the devices of the invention may include reservoirs that either contain buffers, which may be used: (1) as a diluent, (2) to adjust the pH of any liquid within the device, or (3) to wash away unwanted reaction products. These reservoirs may also contain reagents that may be necessary for detecting the analyte gradient. Reservoirs containing buffers or reagents could be positioned next to the zone where their contents would be applied, and could be broken by means included within the device. For example, applying pressure to a particular point may cause pins to be pushed through a sealed bag so that it releases its contents (U.S. Pat. No. 5,356,785). The devices may also contain one or more reservoirs that are of sufficient size and shape to absorb all or substantially all of the liquid that would be applied to or released within the device in the course of performing an assay. These reservoirs may be empty or filled with an absorbent material. Alternatively, excess liquids may be emptied from the device through a drain.

In another aspect, the devices of the invention may be packaged together in a kit with any or all of the diluents or reagents needed to detect a given analyte.

By "analyte" is meant the molecule to be assayed or an analogue or derivative thereof. Analogues or derivatives may be used when they participate in an assay, as one member of a binding pair, in a manner that is substantially equivalent to that of the analyte itself.

The term "operable contact" is meant to define direct or indirect contact between two solid components in any way that allows an aqueous solution to flow in a substantially uninterrupted manner from one of the components to the other component.

Various embodiments of the invention may have one or more of the following advantages. The invention described herein provides a simple, rapid, and effective way to perform quantitative analyses using a portable and disposable test device. This device, the gradient LFD, can perform these analyses over a dynamic range, which can be adjusted to be as narrow or as broad as necessary. The invention establishes a spatial gradient of analyte concentration that may be simultaneously assayed and detected along a test zone. The present invention can provide an indication of analyte concentration without the use of instrumentation.

Other features and advantages of the invention will be apparent from the following description and from the claims.

All publications, patent applications, patents, and other references mentioned herein are incorporated by reference in their entirety.

DETAILED DESCRIPTION

Before describing particular methods and devices of the invention, the general features of the invention will be described. These methods and devices provide the means to establish a liquid front, along which the concentration of an analyte is graded, and to move that front across one or more zones, as illustrated below. As a result, the concentration of any given analyte in any given sample can be determined.

Establishment of an Analyte Gradient

An important feature of the invention is the creation of a liquid front, along which the concentration of the analyte being measured is graded. The analyte gradient can be established, for example, as follows. A sample, which may contain the analyte of interest, is applied to a first pad or chamber, and a diluent, which may be any liquid that does not chemically, or otherwise specifically react with the sample, is applied to a second pad or chamber. The sample application pad or chamber and the diluent application pad or chamber are then brought into operable contact with one another.

The sample and diluent application pads may be any material that is capable of absorbing liquid. These materials include, but are not limited to, high density (or ultra high molecular weight) polyethylene (for example, that manufactured by Porex Technologies Corp., Fairburn, Ga.), olefin or thermoplastic materials, (e.g., polyvinyl chloride, polyvinyl acetate, copolymers of vinyl acetate and vinyl chloride), polyamide, polycarbonate, polystyrene, paper, nitrocellulose, glass fiber, polyester, and nylon.

Figure 5:
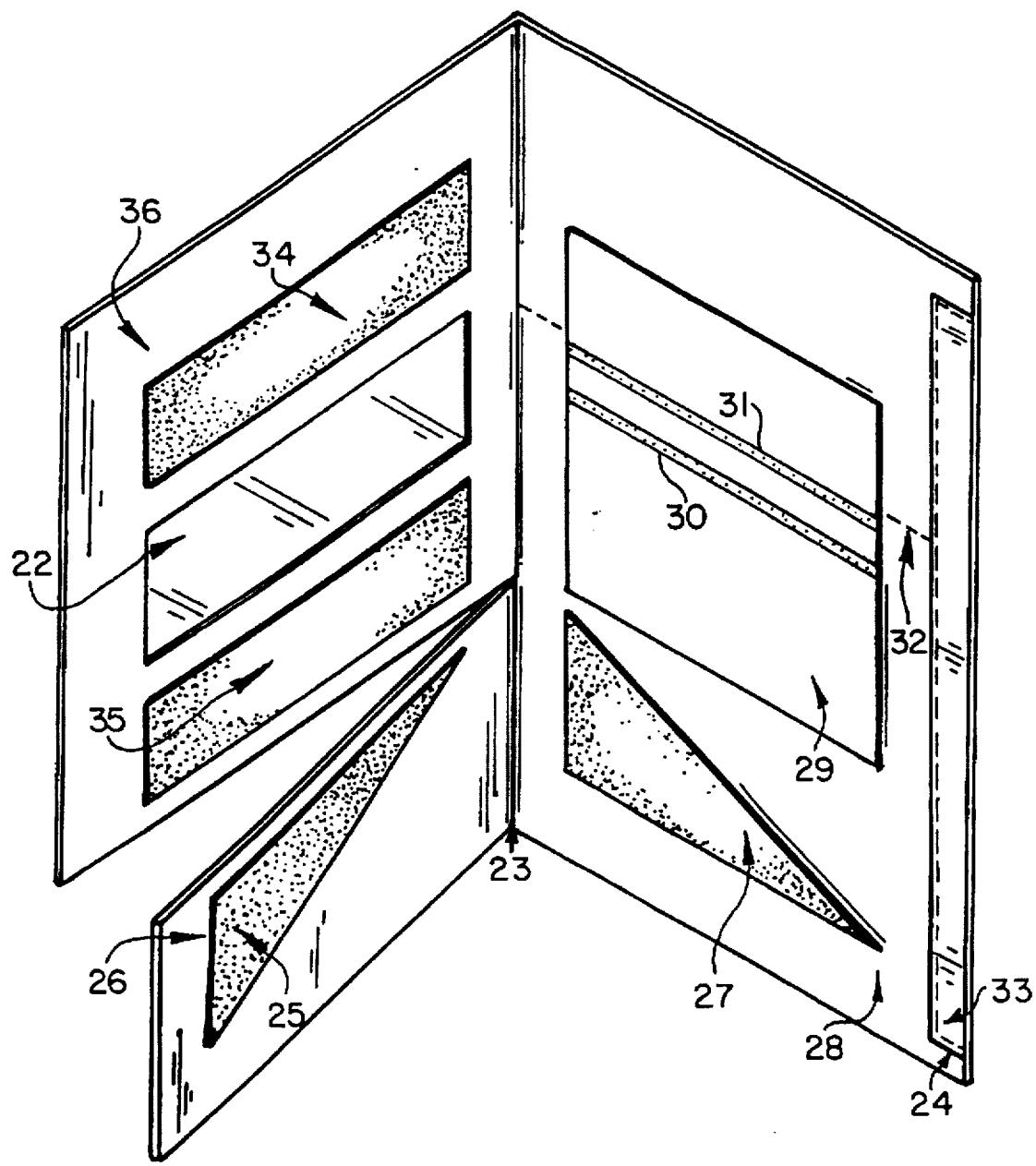
FIG. 5 is an illustration of an example of a gradient reverse lateral flow device, as described in Example 3.

The sample and diluent may be brought into contact, thereby establishing the analyte gradient, in any of a number of ways. For example, the pads can be brought together by pressing on the housing at a strategic point that is designed to collapse under pressure and thus bring these two pads into contact. Alternatively, the device may consist of two surfaces that are joined along one edge, for example, by a hinge. The sample may then be placed on a pad or in a chamber on one surface, e.g., the left-hand surface, and the diluent may be placed in a complementary position on the facing (e.g., the right-hand) surface. To establish the gradient, the opposing surfaces are brought into contact, in much the same way as opposing pages of a book are brought into contact when an open book is closed (FIG. 5; see also WO 95/16207 and WO 95/16208). Another approach entails separating the pads or chambers with a hydrophobic strip or other barrier that effectively separates the sample from the diluent. To establish the gradient, the strip or barrier is removed or slid into another position to allow contact between the sample and diluent. In any event, the sample and diluent are not brought into contact until they have been applied to their respective pads or chambers. Any means by which the sample and diluent are initially separated and subsequently brought together to form a concentration gradient are considered within the scope of the invention.

Following application of the sample and diluent, and establishment of an analyte gradient, flow through the device is achieved by the intrinsic properties of the materials therein. For example, the property may be liquid transfer by capillary action or another mechanism.

The shape of the pads and their orientation are important considerations. If using two smooth-edged, wedge-shaped pads, they are brought together so that the tip of the first wedge is adjacent to the base of the second wedge, and vice-versa. As a consequence, the analyte at the tip of the sample pad will become the most dilute (through contact with the large volume of diluent at the base of the diluent pad) and analyte at the base of the sample pad (through contact with the small volume of diluent at the tip of the pad) will become the least dilute. Between these two points, the concentration of the analyte will be graded. If the analyte gradient is established with two smooth-edged pads, a smoothly graded concentration gradient will be produced. When this gradient is subsequently detected, as described below, the test line that indicates the concentration of analyte will come to an end.

Alternatively, the wedge-shaped pads may have complementary stepped surfaces. In this instance, the concentration gradient that is established by bringing these two pads into contact would also be stepped. The test line that will ultimately be formed to reflect a stepped analyte gradient will end more abruptly than a test line that reflects a smooth analyte gradient. Establishing a stepped analyte gradient would be advantageous when it is necessary to determine only if the concentration of an analyte falls within a particular range: a signal would be apparent at one concentration and absent at the next highest (or lowest) concentration. A stepped analyte gradient is less subjective than a smooth analyte gradient because it is not necessary for the person performing the assay to judge exactly where a tapered line ends.

The analyte gradient can be steep or shallow. A steep gradient would exhibit a greater difference in the concentration of analyte from one end of the gradient front to the other than would a shallow gradient. These gradients are created and can be altered by changing the length and shape (i.e. the angle) of the wedge-shaped sample and diluent pads. For example, long pads that are cut along one edge at a 15° angle would produce a shallower gradient that short pads that are cut along one edge at a 45° angle.

The size and shape of the sample and diluent application pads or chambers will determine both the depth of the concentration gradient (i.e., the magnitude of the dilution; an analyte may be diluted e.g., 1-fold or 100-fold from one end of the gradient to the other), and the dynamic concentration range over which dilution will occur. The spatial orientation of the analyte gradient, whether smooth or stepped, is subsequently maintained as the analyte participates, as the first member of a binding pair, with the second member of a binding pair in the indicator zone or the test zone.

Figure 10:
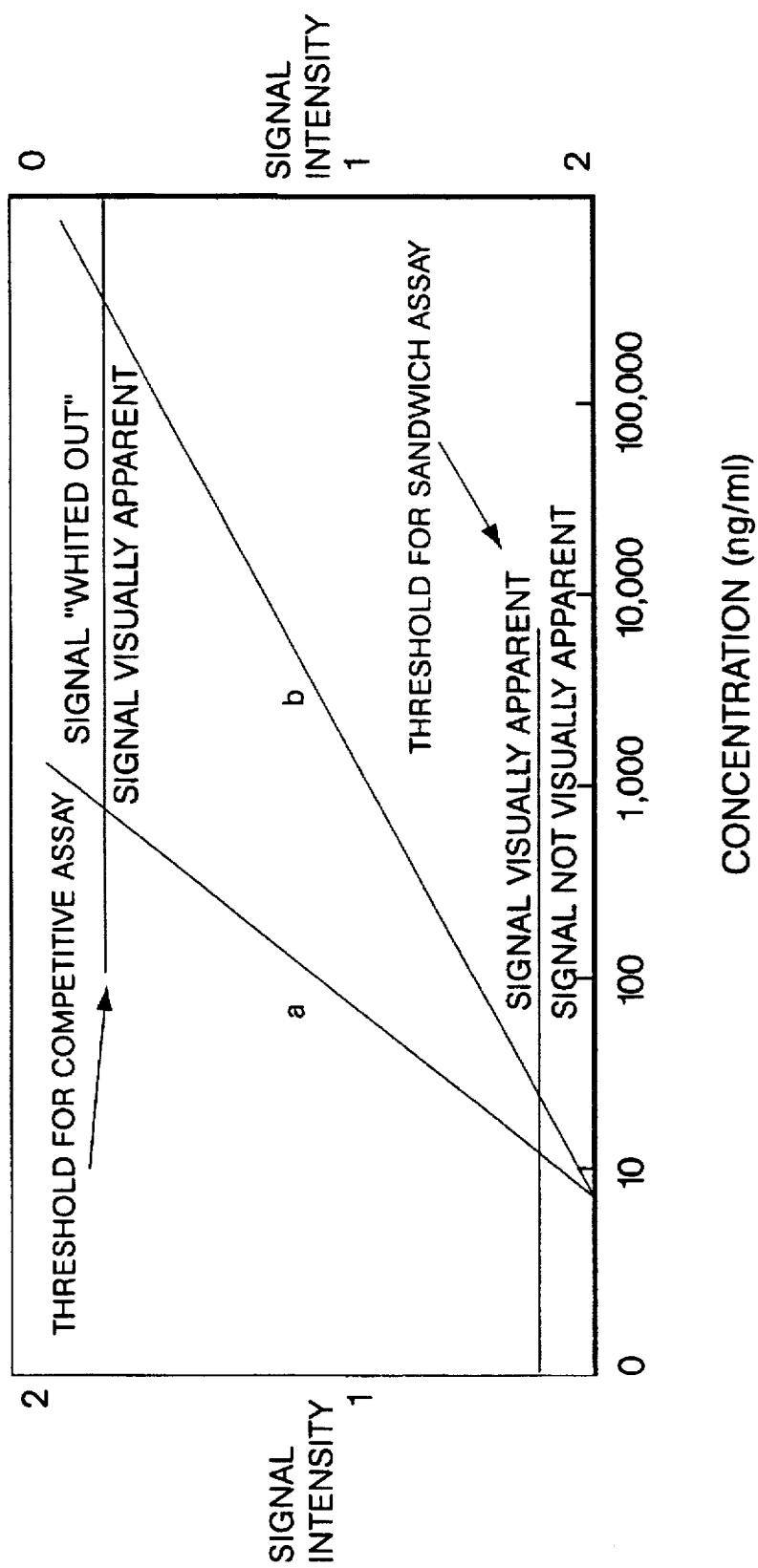
FIG. 10 is a line graph depicting exemplary dose-response curves for a sandwich immunoassay (interpreted from the left-hand Y axis) or a competitive immunoassay (interpreted from the right-hand Y axis) of the invention.

In general, assays are imprecise when a large change in analyte concentration produces only a small change in the signal (curve "b" on FIG. 10). FIG. 10 illustrates how a gradient LFD can be configured to extend the dynamic range of an assay and, at the same time, take full advantage of the desirable precision characteristics of assays that normally have steep or threshold dose-response characteristics (e.g., curve "a" in FIG. 10).

FIG. 10 shows two dose response curves ("a" and "b"). Interpreted from the left-hand Y axis, the curves illustrate example dose-responses for sandwich (e.g., immunometric) assays, which typically display an increase in signal intensity as analyte concentration increases. Interpreted from the right-hand Y axis, the curves illustrate example dose-responses for competitive assay, which typically result in a decrease in signal intensity as analyte concentration increases. Curve "a" shows a steep dose response, which is normally associated with high precision and narrow dynamic range, while curve "b" shows a shallow dose response, which is normally associated with lower precision but a broad dynamic range. The loss of precision in moving from curve "a" to curve "b" can be seen by extrapolating identical variations in signal intensity (from the Y axis) into the corresponding concentration differences along the X axis using each of the two curves. In most analytical situations, it would be advantageous to maintain the precision afforded by curve "a" but at the same time have the ability to guantitate over a wide dynamic range, as shown in curve "b". To accomplish this in practice, a series of sample dilutions could be analyzed using the assay of curve "a" with the results subsequently corrected to account for the dilutions used.

Lateral flow assays provide qualitative information, i.e., whether an analyte is above or below a defined concentration. This qualitative result is visually interpreted by either the presence or absence of a test line on the device following the analysis. FIG. 10 illustrates the portion of the dose response curves where a signal either begins to become visible or where the signal becomes invisible ("whited out"). For a sandwich assay, the sensitivity would be defined as the point at which a visible signal can first be observed, while for a competitive assays, the sensitivity is defined as the point at which a visible signal can no longer be seen. An assay exhibiting curve "a" provides a sharper and more precise interpretation threshold between positive and negative than curve "b" and thus provides a more desirable threshold assay. The sensitivity of particular assays is a function of the relative affinity and concentration of the various reagents and the times during which particular reagents and analyte are in contact with each other. Those skilled in the art are familiar with methods for optimizing and characterizing the sensitivity and dose-response characteristics of conventional assays used in lateral flow devices. A sandwich assay having the dose response characteristics of a curve "a" could be used to produce a conventional lateral flow device that has a sensitivity of 10 ng/ml. Thus, if the sample contains analyte at 10 ng/ml or greater, there will be sufficient analyte to react with the fixed test line and to capture sufficient signaling substance to result in a detectable signal. The detectable signal will be of the same intensity across the width of the test line since the analyte normally travels across the width of the test line in a uniform concentration. If the sample contains analyte at 100 ng/ml, a signal would develop at the test line and the results would still be interpreted the same, analyte is detected. By performing a series of dilutions on this sample one could determine that it takes a tenfold dilution to reach the sensitivity limit of the LFD and therefore the sample contains about 100 ng/ml of analyte.

Figure 12:
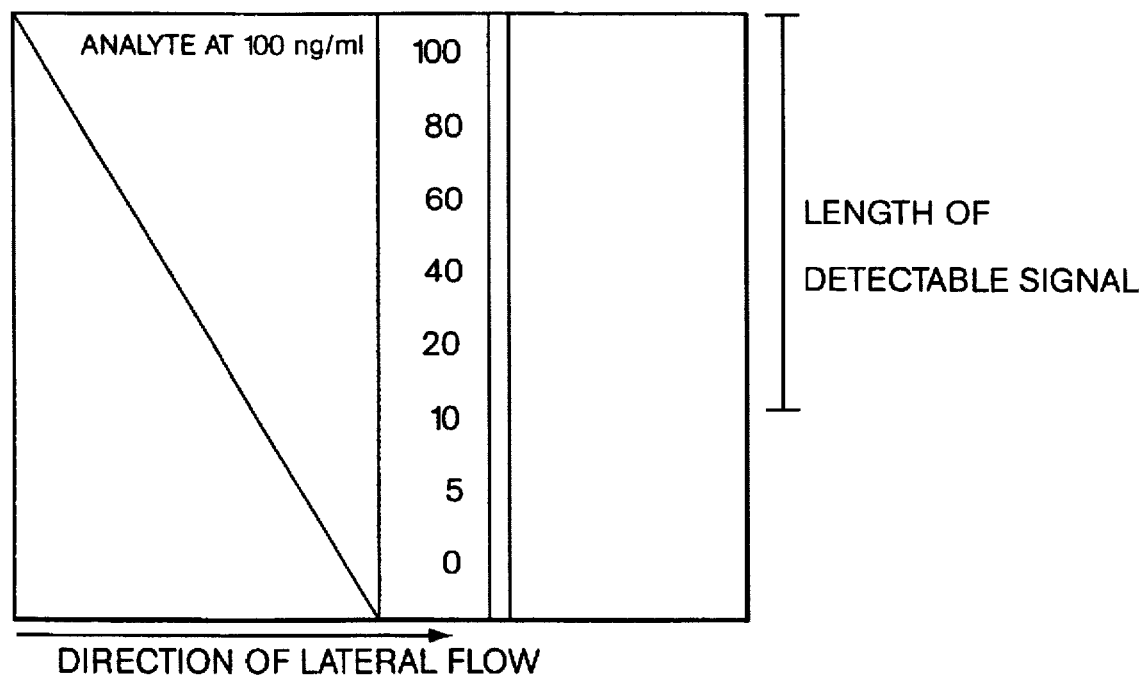
FIG. 12 is a schematic diagram illustrating a gradient lateral flow device that has been configured to produce a detectable signal above 10 ng/ml of analyte. The vertical numerical display reflects the concentration of the analyte at the gradient front.

The gradient lateral flow device provides a means of using curve "a" while at the same time creating a gradient of sample dilution across a pre-defined dynamic range (defined by the size and shape of the complementary sample and dilution pads or chambers). Thus, for a sample containing an analyte at 100 ng/ml, the test line will remain visible across a distance of the analyte gradient that is equivalent to a 10-fold drop in concentration (FIG. 12). Beyond that distance, the analyte concentration will be below the threshold of the assay and therefore, no test line will be detected. The higher the analyte concentration, the further into the gradient the analyte must move to be diluted to the detection limit of the assay, and therefore the greater the length of detectable test line following the assay. For competitive assays, the same situation applies, except that the detectable line will be at its longest for no or low analyte concentration and increasing concentrations of analyte in the sample will result in decreasing lengths of detectable test line following the assay.

The Indicator Zone

The analyte, present along the concentration gradient described above, will move downstream as a front and may next contact the indicator zone, which contains a binding member. The binding member in the indicator zone interacts with the analyte in the sample and becomes mobile upon contact with the moving analyte gradient front. The length of the indicator zone will be approximately the same as the length of the analyte gradient front, and the two will be parallel to one another. The indicator zone may also contain an appropriate signalling substance such colored latex beads, or silica, or liposomes that have encapsulated chemiluminescors (e.g., luciferin) or chromophores (e.g., dyes, or pigments). The signalling substance may also consist of a colloid system containing, for example, colloidal carbon or a dispersion of a metal such as gold or silver, which may be associated with the mobile binding member. Alternatively, the binding member may be associated with a signalling substance that is not particulate such as a dye, a fluorophore, enzyme, or a chemiluminescor.

Examples of binding pairs that may form in the indicator zone (either of which could be the analyte or the binding member) are: antigen-antibody, antigen-antibody fragment, antibody-hapten, antibody-cell, antibody-cell fragment, nucleic acid-nucleic acid, receptor-ligand, enzyme-substrate, biotin-avidin, lectin-carbohydrate, Protein A-immunoglobulin, and molecularly imprinted polymer (MIP)-imprinted compound.

Because of the properties of the materials within the gradient LFD, the analyte will move through the indicator zone, mobilizing the binding member therein, and presenting it for subsequent reaction (or non-reaction) with the fixed binding member present in the test zone.

The Test Zone

The analyte gradient may move into the indicator zone, as described above, and then downstream to the test zone. Alternatively, the analyte gradient may flow directly into the test zone. In the later instance, the concentration of the analyte in the sample may be determined immediately, or after subsequent contact between the test zone and the indicator zone. In any event, the test zone will contain a fixed binding member that reacts either with the analyte, or with the mobile binding member that has been carried to the test zone from the indicator zone.

The gradient LFD may be used to carry out assays analogous to those referred to as "competitive" or "sandwich" (immunometric) type immunoassays. "Competitive" assays are those in which a labeled antigen or antibody competes with the antigen or antibody being assayed for an immunological binding site on a solid phase, for example, a bead or pad. The "sandwich" assay differs from this in that the antibody or antigen being assayed is sandwiched between a solid surface treated with one member of a complementary binding pair and either the same or a different complementary binding member that has been coupled to a detectable label.

The Gradient LFD can be used to perform both competitive and sandwich type assays. Typically, large molecules (those greater than approximately 5000 Da) will be assayed with the gradient LFD using a sandwich type configuration. This leads to the presence of a test line when the analyte concentration is above a specified threshold concentration. For lower molecular weight compounds, a competitive type configuration is used, which may result in an inhibition or "white out" of a test line when the analyte concentration is above a specified threshold. However, certain competitive assays have been developed in which the test line, rather than being inhibited, becomes visible (see, e.g., U.S. Pat. No. 5,527,686). In either event, interpretation of the concentration of analyte will be made by inspecting the line and determining at what point it becomes apparent or disappears.

The detectable test line forms in the test zone as the result of the specific association between the fixed binding member in the test zone and either the analyte, or the mobile binding member that has interacted with the analyte in the indicator zone. The binding member in the test zone may consist of any of the agents specified above as binding members. Similarly, it may be associated with the same signalling substances described above.

The Control Zone

A control zone that contains a line, or some other configuration, such as a spot, that becomes detectable in a manner that is independent of the analyte gradient can also be included in the device. Preferably, the control zone is in the vicinity of the test zone and consists of an immobilized binding member that reacts with some portion of a binding member, or signalling substance, from the indicator zone.

The test zone and the control zone may be covered with a clear or translucent cover to facilitate visualizing the signal generated. The cover may be uniform, or it may be punctuated by, for example, lines or bars that facilitate determining whether the concentration of the analyte falls within a particular range.

EXAMPLE I

There is described below the structure and operation of a particular gradient LFD of the invention, which is used to conduct a sandwich-type assay.

Structure

Figure 1:
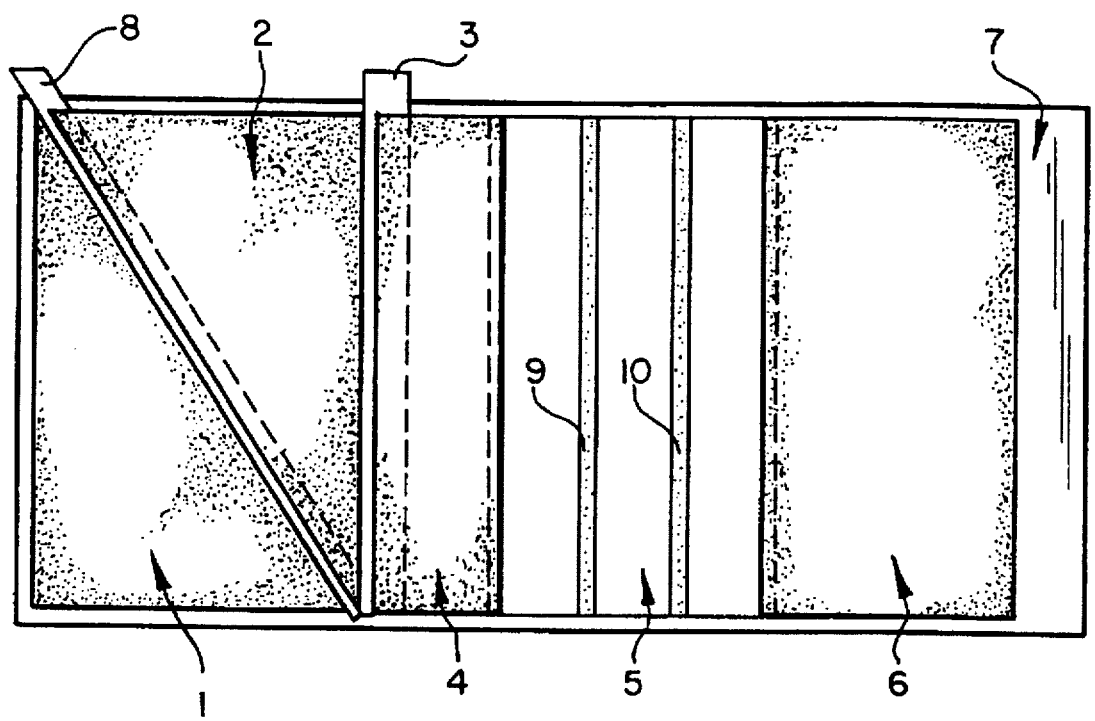
FIG. 1 is an illustration of an example of a gradient lateral flow device, as described in Example 1. The upper housing has been removed.

FIG. 1 is an illustration of a gradient LFD, showing a top view of the device from which the upper housing has been removed. This device includes a wedge-shaped pad of absorbent paper (1; e.g., absorbent grade 470 paper from Schleicher and Schuell, Keene, N.H.) to which diluent is applied, and a complementary wedge-shaped pad (2), of the same or similar material, to which sample is applied. The diluent pad (1) is separated from the sample pad (2) by a strip of hydrophobic polystyrene (8; Filter, Flow, and Seal Inc., Claymont, Del.) that may be displaced. The indicator zone consists of a pad of polyester (4; Ahlstrom Filtration, Mt. Holly Springs, Pa.) that is the same width as the sample application pad (2), from which it is separated by a second strip of hydrophobic polystyrene (3) that may also be displaced. The hydrophobic polystyrene strip (8), which separates the diluent pad (1) from the sample pad (2), projects from the housing as a tab, as does the hydrophobic polystyrene strip (3), which separates the sample pad (2) from the indicator zone (4). This arrangement allows the strips to be manually displaced by pulling on the exposed tabs. The indicator pad (4) is in direct contact with and slightly overlapping, a piece of nitrocellulose membrane (5; e.g., 15 µm fast flow nitrocellulose; Millipore Corporation, Bedford, Mass.) that contains two zones of immobilized reagents: the test zone (9) and the optional control zone (10). Nitrocellulose membrane 5 is in direct contact with, and slightly overlapped by, an absorbent pad (6) that serves as a sink for excess sample and diluent that has been wicked from pads 1 and 2 through pads 4 and 5. The absorbent elements described are oriented and fixed in place along a strip of adhesive-backed plastic (7).

Figure 2:
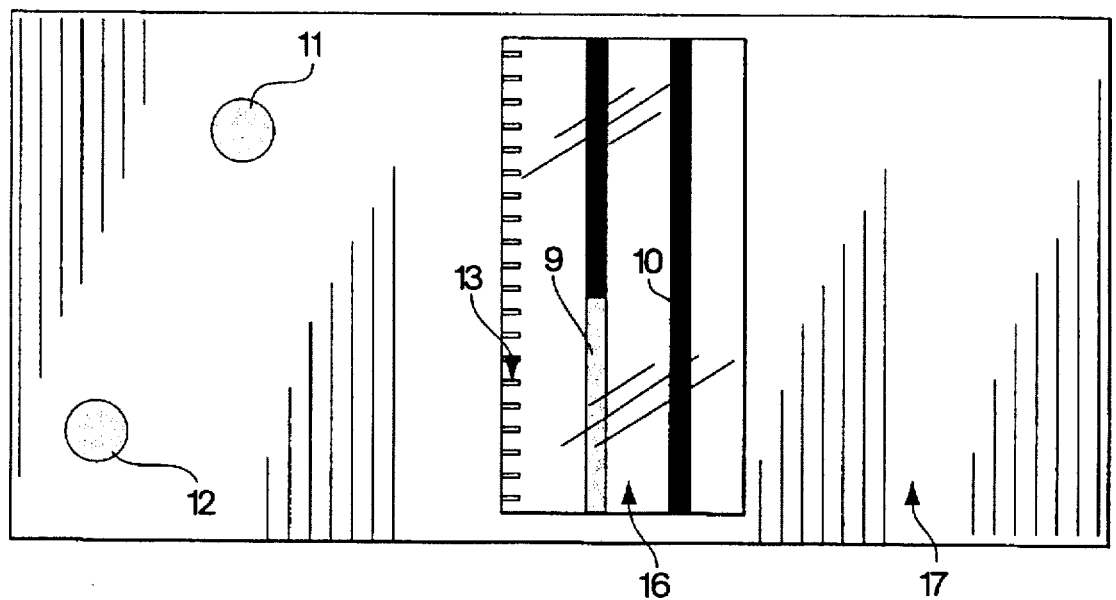
FIG. 2 is an illustration of the device shown in FIG. 1, with the upper housing, as it would appear following a sandwich-type assay, such as the assay described in Example 1.

The upper surface of the housing (17) of the gradient LFD is shown in FIG. 2. Sample is introduced through a sample port (11) and diluent is introduced through a diluent port (12). The housing contains a window (16) that exposes the nitrocellulose membrane (5) for viewing. A scale (13) can be employed as an aid to quantifying the concentration of analyte. Following analysis of a sample, a visual reaction product will be evident in the test zone (9) and in the control zone (10).

To manufacture the device, a 4 cm×8 cm plastic card (7) is covered with double-sided adhesive tape (Adhesives Research Inc., Glen Rock, Pa.), and the various absorbent members are attached to the adhesive-coated plastic card. The nitrocellulose (5; 4 cm×2 cm), whose left 4 cm side is located parallel to and 4 cm from the left edge of the plastic card, is adhered first. The indicator zone (4; 4 cm×1 cm) is adhered to the left of the nitrocellulose pad (5) and overlaps it by 2 mm. The sample application pad (2; a right triangular pad 4 cm×2 cm×4.47 cm) is adhered to the left of (4) and overlaps it by 2 mm along its 4 cm edge. The strip of hydrophobic polystyrene (3) is placed between the overlap of the sample application pad (2) and (4) to prevent contact between the pads. The diluent application pad (1; a right triangular pad 4 cm×2 cm×4.47 cm) is located to the left of (2) and overlaps it by 2 mm along the 4.47 cm edge. The strip of hydrophobic polystyrene (8) is placed between the diluent application pad (1) and the sample application pad (2) to prevent contact of the pads. The sink pad (6; 4 cm×2 cm) is adhered to the right of the nitrocellulose pad (5) and overlaps it by 2 mm along its 4 cm edge. The card assembly described is then placed into a plastic housing (17) that: positions the sample port (11) over the sample application pad (2); positions the diluent application port (12) over the diluent application pad (1); and positions the viewing window (16) over the test zone (9) and control zone (10) of the nitrocellulose membrane (5).

Operation

The device illustrated in FIG. 1 may be used to quantify a human immunoglobulin molecule, such as an antibody of the IgG type. To prepare the device for this assay, the pads within the various zones are treated as follows.

The absorbent pad within the indicator zone (4) is pre-blocked for 30 minutes with a solution consisting of 50 mM phosphate, 0.5% PVA, 0.5% BSA, and 0.1% Triton X-100 (Ph 7.4). Goat anti-human IgG colloidal gold conjugate (Sigma Chemical Co., St. Louis, Mo.) having an optical density at 540 nm of 15 absorbance units is applied across the entire 4 cm width of the indicator zone pad 4 in a line 2 mm wide, and at a rate of 4 µl gold reagent per linear cm using a TLC sprayer (Camag, Wilmington, N.C.). The 2 mm wide line runs perpendicular to the center of the 1 cm edge of the indicator zone pad (4).

The sample application pad 2 is pre-blocked with a solution consisting of 0.01M sodium borate and 0.1% Triton-X-100 (pH 8.6). The sample application pad (2) is then dried overnight at 37° C.

The reagents that are found at the test zone (9) and control zone (10) can be applied to 15 µm fast flow nitrocellulose (5; 4 cm×2 cm) with a TLC sprayer (Camag, Wilmington, N.C.). The reagent applied to the test zone is goat anti-human IgG (Sigma Chemical Co., St. Louis, Mo.) which is diluted in phosphate buffer and applied across the entire 4 cm width of the nitrocellulose in a line 1 mm wide and at a concentration of 2 µg of antibody per linear cm. The 1 mm wide line runs perpendicular to the 2 cm edge of the nitrocellulose (5) at a distance of 8 mm from the 4 cm wide edge that contacts the indicator zone pad (4). The reagent applied to the control zone (10) is rabbit anti-goat IgG (Sigma Chemical Co., St. Louis, Mo.) which is diluted in phosphate buffer and applied across the entire 4 cm width of the nitrocellulose in a line 1 mm wide and at a concentration of 4 µg of antibody per linear cm. The 1 mm wide line runs perpendicular to the 2 cm edge of the nitrocellulose (5) element at a distance of 12 mm from the 4 cm wide edge that contacts the indicator zone pad (4). The nitrocellulose (5) is then dried overnight at 37° C.

The concentration of human IgG in a serum sample is quantified by first adding 300 µl of serum to the sample application port and 300 µl of phosphate buffer to the diluent application port. To establish an analyte gradient, strip 8 is withdrawn from the side of the housing, allowing the diluent application pad (1) to contact the sample application pad (2). To initiate the assay, strip 3 is withdrawn from device allowing sample application pad (2) to contact the indicator zone (4). Thus, initiating the flow of the graded analyte front laterally through the indicator zone (4), the test zone (9), the control zone (10), and the sink (6). As the liquid front moves through the indicator zone, the goat anti-human IgG-colloidal gold is rehydrated and carried laterally toward the test zone (9). As this occurs, the human IgG in the serum sample binds to the anti-human IgG colloidal gold conjugate. The concentration of colloidal gold across the gradient front remains constant. However, the amount of human IgG that is bound to the anti-human IgG on the gold particles will be directly proportional to its concentration at any given position along the gradient front. As the gold particles pass across the immobilized anti-human IgG located in the test zone (9), the antibody-gold conjugate particles that have bound human IgG will be captured and concentrated. A visual line will form in the test zone (9) that is proportional in length to the concentration of human IgG in the serum sample. The concentration of IgG is interpreted from a reference scale (13), which is placed on the housing, at the edge of the viewing window. After passing the test zone, the gold front continues to move laterally across the control zone, which contains immobilized rabbit anti-goat IgG. As the gold passes across the anti-goat IgG located in the control zone (10), gold particles, which all carry the goat anti-human IgG, are captured and concentrated. A visual line forms across the entire control zone (10), indicating that the assay has functioned properly. The excess liquid and reagents will continue to move laterally across the device and collect in the sink (6).

When used as described above, the gradient LFD detects antibodies of the IgG type in the range of 25–25,000 µg/ml.

EXAMPLE 2

There is described below the structure and operation of a particular gradient LFD of the invention, which is used to conduct a competitive-type assay.

Structure

Figure 3:
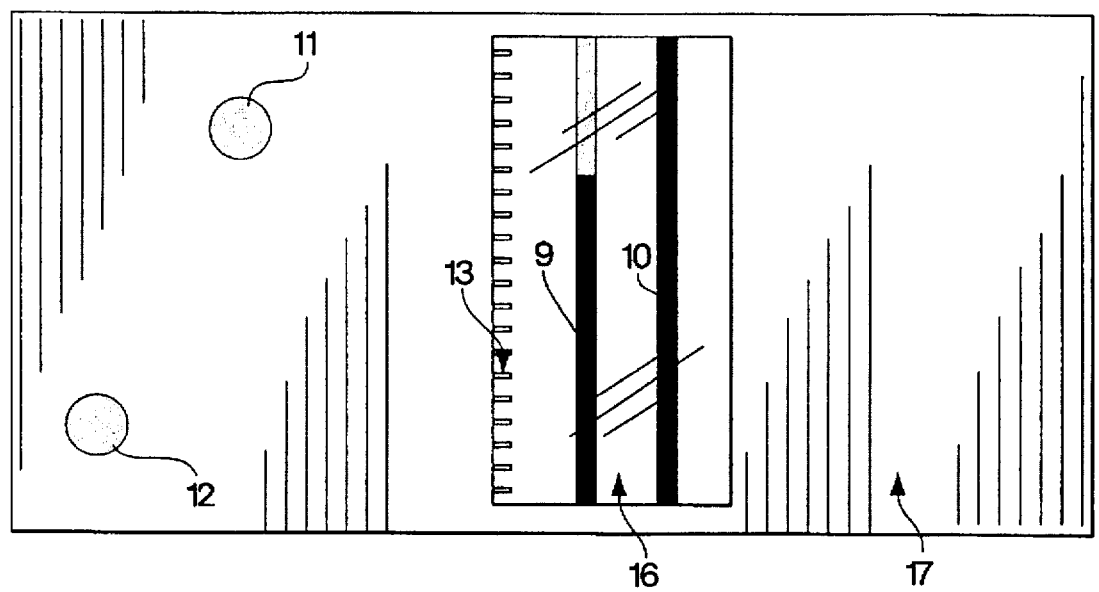
FIG. 3 is an illustration of the device shown in FIG. 1, with the upper housing, as it would appear following a competitive-type assay, such as the assay described in Example 2.
Figure 4:
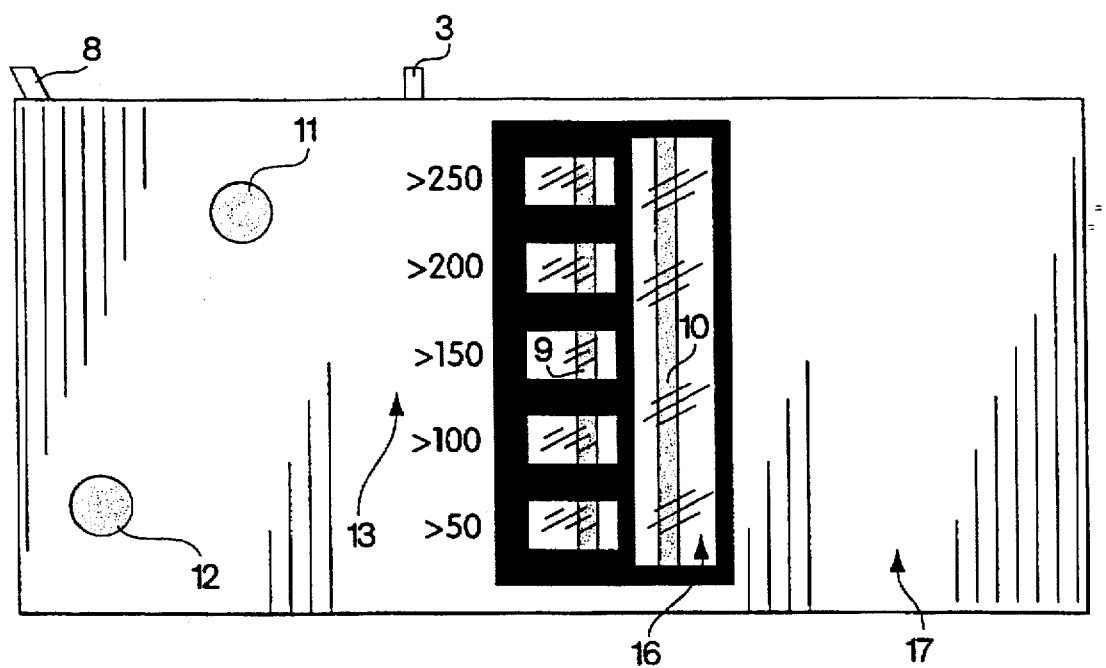
FIG. 4 is an illustration of the upper surface of a gradient lateral flow device in which the viewing window is divided.

The structure of the device described here, which is used to conduct a competitive-type assay, is identical to the device described in Example 1 (and shown in FIG. 1). However, with the device used in this instance, the disappearance (rather than the appearance) of the test line indicates the concentration of analyte in the sample (see FIG. 3).

Operation

The gradient LFD may be used to quantify the concentration of the herbicide atrazine in a water sample. In this instance, the absorbent pad within the indicator zone (4) is pre-blocked for 30 minutes with a solution consisting of 50 mM phosphate, 0.5% PVA, 0.5% BSA, and 0.1% (v/v) Triton X-100 (pH 7.4). The pad is then dried overnight at 37° C. The mouse anti-atrazine IgG-colloidal gold conjugate (Biostride Inc., Palo Alto, Calif.) having an optical density at 540 nm of 15 absorbance units is applied across the entire 4 cm width of the indicator zone pad (4) in a line 2 mm wide, and at a rate of 4 µl gold reagent per linear cm using a TLC sprayer (Camag, Wilmington, N.C.). The 2 mm wide line runs perpendicular to the center of the 1 cm edge of the indicator zone pad (4).

The sample application pad (2) is pre-blocked with a solution consisting of 0.01M sodium borate and 0.1% Triton-X-100 (pH 8.6). The sample application pad (2) is then dried overnight at 37° C.

The reagents that are found at the test zone (9) and control zone (10) can be applied to 15 µm fast flow nitrocellulose (5; 4 cm×2 cm) with a TLC sprayer (Camag, Wilmington, N.C.). The reagent applied to the test zone is atrazine-BSA (Biostride Inc., Palo Alto, Calif.) which is diluted in phosphate buffer and applied across the entire 4 cm width of the nitrocellulose in a line 1 mm wide and at a concentration of 2 µg of antibody per linear cm. The 1 mm wide line runs perpendicular to the 2 cm edge of the nitrocellulose (5) at a distance of 8 mm from the 4 cm wide edge that contacts the indicator zone pad (4). The reagent applied to the control zone (10) is rabbit anti-mouse IgG (Sigma Chemical Co., St. Louis, Mo.) which is diluted in phosphate buffer and applied across the entire 4 cm width of the nitrocellulose in a line 1 mm wide and at a concentration of 4 µg of antibody per linear cm. The 1 mm wide line runs perpendicular to the 2 cm edge of the nitrocellulose (5) at a distance of 12 mm from the 4 cm wide edge that contacts the indicator zone pad (4). The nitrocellulose (5) is then dried overnight at 37° C.

The concentration of atrazine in the water sample is quantified by adding 300 µl of the water sample to the sample application port and 300 µl of phosphate buffer to the diluent application port. To establish an analyte gradient, strip 8 is withdrawn from the side of the housing, allowing the diluent application pad (1) to contact the sample application pad (2). To initiate the assay, strip 3 is withdrawn from device allowing sample application pad (2) to contact the indicator zone (4). Thus, initiating the flow of the graded analyte front laterally through the indicator zone (4), the test zone (9), the control zone (10), and the sink (6). As the liquid front moves through the indicator zone, the mouse anti-atrazine IgG-colloidal gold is rehydrated and carried laterally toward the test zone (9). The atrazine in the water sample binds to the anti-atrazine IgG-colloidal gold. The concentration of colloidal gold across the gradient front remains constant. However, the amount of atrazine that is bound to the anti-atrazine IgG on the gold particles will be directly proportional to its concentration at any given position along the gradient front. As the gold particles pass across the atrazine-BSA located in the test zone (9), gold particles carrying the atrazine blocked antibody will pass across the test zone without binding to the immobilized atrazine-BSA conjugate. A visual line will form in the test zone (9) that is inversely proportional in length to the concentration of atrazine in the water sample. The concentration of atrazine is interpreted from a reference scale (13), which is placed on the housing, at the edge of the viewing window. After passing the test zone, the gold front continues to move laterally across the control zone, which contains immobilized rabbit anti-mouse IgG. As the gold passes across the anti-mouse IgG located in the control zone (10), gold particles, which all carry the mouse anti-atrazine IgG, are captured and concentrated. A visual line forms across the entire control zone (10), indicating that the assay has functioned properly. The excess liquid and reagents will continue to move laterally across the device and collect in the sink (6).

When used as described above, the gradient LFD detects atrazine in the range of 5–500 ng/ml.

EXAMPLE 3

There is described below the structure and operation of a particular gradient LFD of the invention, which functions as a gradient reverse flow device (GRFD).

Structure

FIG. 5 shows a view of a Gradient Reverse Flow Device (GRFD). This device includes a right wedge-shaped pad (4 cm×2 cm×4.47 cm) of absorbent material (27) such as absorbent paper (e.g., grade 470 paper; Schleicher and Schuell, Keene, N.H.) which serves as the diluent application pad. Similarly, the sample application pad (25) is a wedge-shaped pad (4 cm×2 cm×4.47 cm) of absorbent material such as absorbent paper (e.g., grade 470 paper; Schleicher and Schuell, Keene, N.H.) which serves as the sample application pad. The sample application pad (25) is attached to a non-absorbent page of coated cardboard (26; 3 cm×5 cm) that is attached through a hinge (23) to the opposing page (28). The sample application pad (25) can be brought into contact with both the diluent application pad (27) and the nitrocellulose membrane (29; 4 cm×2 cm) by first removing a strip of protective paper (33), thus exposing the underlying adhesive strip (24). The bottom of the left-hand page (26) may then fold down over the right-hand page (28) so that the bottom left-hand page (26) is held in place by the adhesive strip (24) and the diluent application pad (27), the sample application pad (25), and the nitrocellulose pad (29), are positioned so that their edges are all in contact and overlapping by approximately 2 mm. The indicator zone (34; 4 cm×1.5 cm) is comprised of a rectangular piece of polyester (Ahlstrom Filtration, Mt. Holly Springs, Pa.) and is positioned on the top of the left-hand page (36; 4.5 cm×5 cm) such that when the top of the left-hand page (36) and the right-hand page (28) are brought together, the indicator zone (34) will be in direct contact with and overlapping, by approximately 2 mm, the nitrocellulose pad (29; Millipore Corporation, Bedford, Mass.). Also positioned on the top left-hand page (36) is an absorbent pad (35; 4 cm×0.5 cm) which can be brought into direct contact with the nitrocellulose pad (29), by adhering the edge of the top left-hand page (36) with the adhesive strip (24) on the right-hand page (28). The absorbent pad (35) will completely overlap the nitrocellulose pad (29). A window (22) is positioned on the top left-hand page (36) such that the line that will develop in the test zone (31) and the line that will develop in the control zone (30) can be viewed following the assay. A reverse line (32) printed on the right-hand page (28) provides a reference point indicating that a certain volume of liquid has passed across the test line and that the flow of liquid should be reversed by folding the top left-hand page (36) onto the right-hand page (28), as previously described. Determining the volume of liquid that will optimally pass the reverse line is determined empirically for each assay.

Operation

The device illustrated in FIG. 5 may be used to quantify a human immunoglobulin molecule, such as an antibody of the IgG type. To prepare the device for this assay the pads within the various zones are treated as follows.

The indicator zone (34) is pre-blocked for 30 minutes with a solution consisting of 50 mM phosphate, 0.5% PVA, 0.5% BSA, and 0.1% Triton X-100 (pH 7.4). A goat anti-human IgG colloidal gold conjugate (Sigma Chemical Co., St. Louis, Mo.) having an optical density at 540 nm of 15 absorbance units is applied across the entire 4 cm width of the indicator zone (34) in a line 2 mm wide and at a rate of 4 µl of gold reagent per linear cm using a TLC sprayer (Camag, Wilmington, N.C.). The 2 mm wide line runs perpendicular to the 1.5 cm edge of the indicator zone (34) centered on a point 3 mm from the edge of the pad that is in opposable contact with the nitrocellulose pad (29).

The sample application pad (25) is pre-blocked with a solution consisting of 0.01M sodium borate and 0.1% Triton X-100 (pH 8.6). The sample application pad is then dried overnight at 37° C.

The reagents within the test zone (31) and the control zone (30) can be applied to 15 µm fast flow nitrocellulose (29; 4 cm×2.5 cm) with a TLC sprayer (Camag, Wilmington, N.C.). The reagent applied to the test zone (31) to create the test line is goat anti-human IgG (Sigma Chemical Co., St. Louis, Mo.). The antibody is diluted in phosphate buffer and applied across the entire 4 cm width of the zone in a line that is 1 mm wide. The concentration of this antibody is 2 µg per linear cm. The test line runs perpendicular to the 2.5 cm edge of nitrocellulose pad (29) at a distance of 10 mm from the 4 cm wide edge that is in opposable contact with the sample application pad (25). The reagent applied to the control zone (30), rabbit anti-goat IgG (Sigma Chemical Co., St. Louis, Mo.), is diluted in phosphate buffer and applied across the entire 4 cm width of the zone in a line that is 1 mm wide. The concentration of this antibody is also 2 µg per linear cm. Similarly, the 1 mm wide control line runs perpendicular to the 2.5 cm edge of the nitrocellulose pad (29), but at a distance of 14 mm from the 4 cm wide edge that is in opposable contact with the sample application pad (25). The test zone and the control zones are dried overnight at 37° C.

The concentration of human IgG in a serum sample is quantified by first adding 300 µl of serum to the sample application pad (25) and 300 µl of phosphate buffer to the diluent application pad (27). To establish an analyte gradient and to initiate flow of the gradient through the nitrocellulose membrane, sample application pad (25) is brought into contact with diluent application pad (27) and the nitrocellulose pad (29). This is accomplished by exposing an adhesive strip (24) by removing an overlying protective paper (33) and then folding and adhering the bottom half of the left-hand page (26) to the right-hand page (28) along their outer edges. The dry reagent in the indicator zone (34) is then rehydrated by adding 200 µl of phosphate buffer.

As the liquid front of the analyte gradient passes across the control zone (30) and test zone (31), any human IgG in the sample will be captured by the anti-human IgG antibody, fixed at the test zone (31), in an amount that is directly proportional to its position across the gradient front. When the liquid gradient front reaches the reverse line (32), the indicator zone (34) is brought into contact with the nitrocellulose pad (29) and the absorbent pad (35) is brought into contact with the nitrocellulose membrane (29) by folding the top half of the left-hand page (36) onto the right-hand page (28) and adhering the two pages together at their edges along the adhesive strip (24). This initiates reverse flow whereby the goat anti-human IgG-colloidal gold in the indicator zone (34) moves through the nitrocellulose pad (29), across the test zone (31) and the control zone (30) and into the absorbent pad (35). As the goat anti-human IgG-colloidal gold passes across the test zone (31) it will bind to any human IgG that had previously been captured and concentrated by the goat anti-human IgG fixed at the test zone. A visual line will form that is proportional in length to the concentration of human IgG in the serum sample. The concentration of IgG is interpreted from a reference scale, which is placed along the outside edge of the viewing window (22). After passing the test zone, the gold front continues to move laterally across the control zone (30) which contains immobilized rabbit anti-goat IgG. As the gold passes across the anti-goat IgG located in the control zone, gold particles which all carry the goat anti-human IgG are captured and concentrated. A visual line forms across the entire control zone indicating that the assay has functioned properly. The excess liquid and reagents will continue to move through the membrane and into the absorbent pad (35).

Other Embodiments

Still further embodiments are possible.

Figure 6:
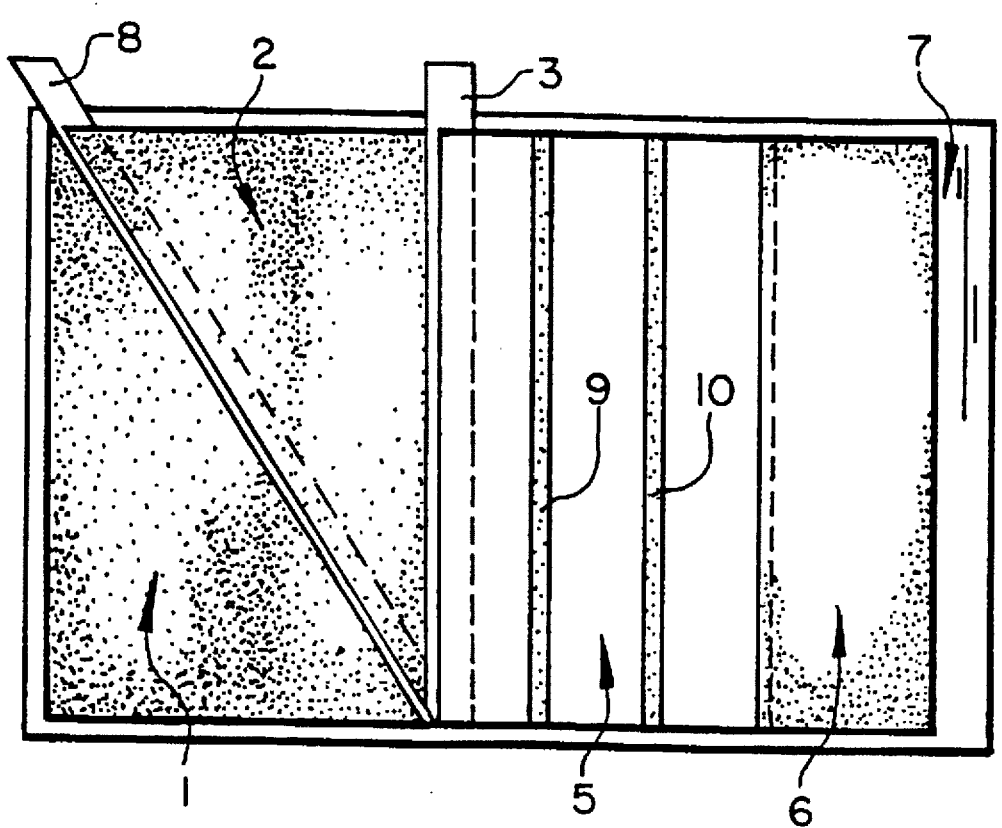
FIG. 6 is an illustration of an example of a gradient lateral flow device that does not contain an indicator zone. The upper housing has been removed.

In FIG. 6 there is shown a gradient lateral flow device wherein the indicator zone is absent. In this device, an analyte gradient is established and brought directly into contact with a nitrocellulose pad on which a test line and a control line have been formed.

Figure 7:
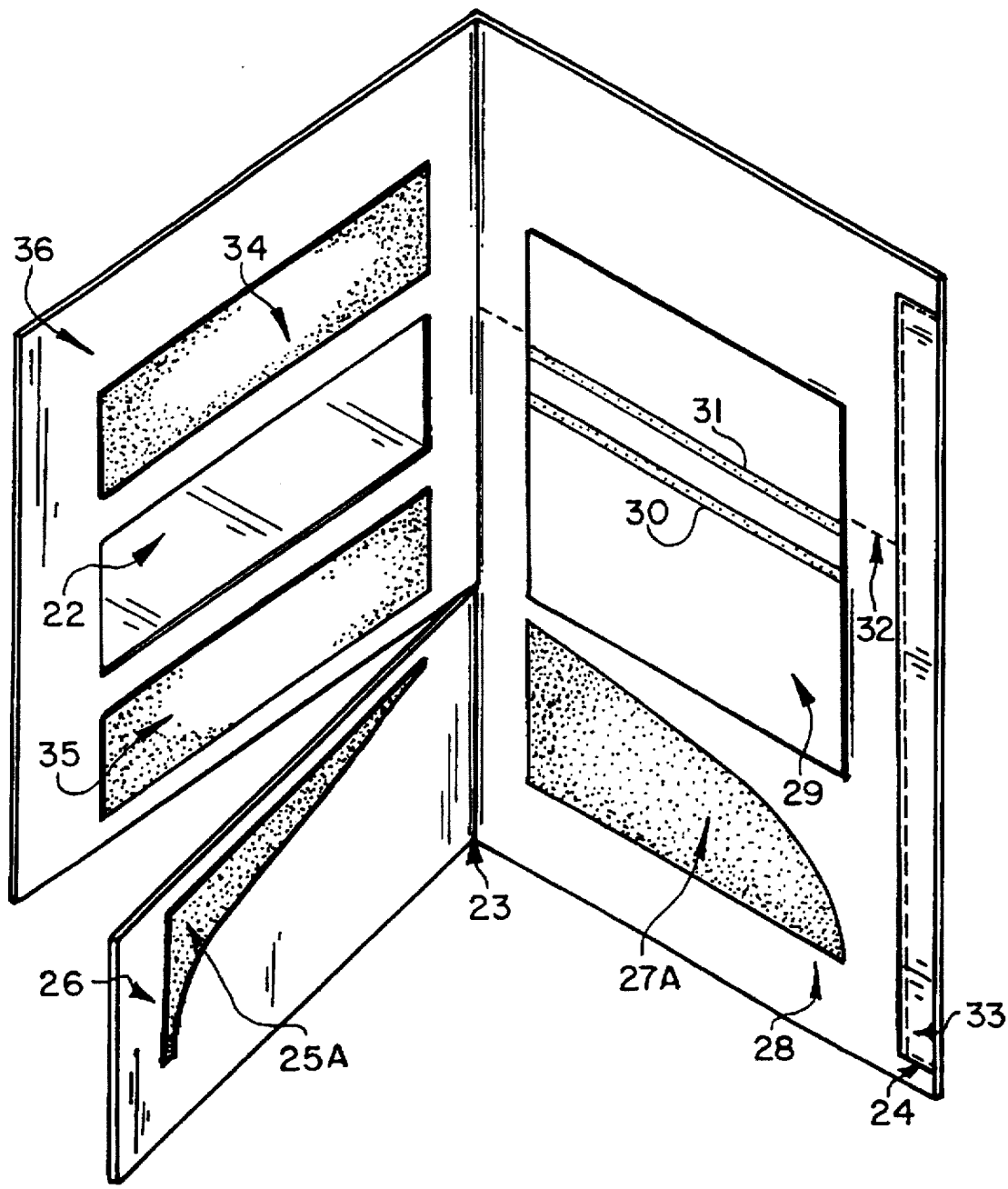
FIG. 7 is an illustration of an example of a gradient lateral flow device that could be used to establish a non-linear analyte gradient.

In FIG. 7 there is shown a gradient lateral flow device wherein a non-linear analyte gradient is established. In this configuration, the complementary sample and diluent application pads are attached to surfaces that can be brought into operable contact by folding them toward one another. In FIG. 7, the sample application pad (25A) is attached to the bottom left-hand page (26) and the diluent application pad (27A) is attached to the right-hand page (28).

Figure 8:
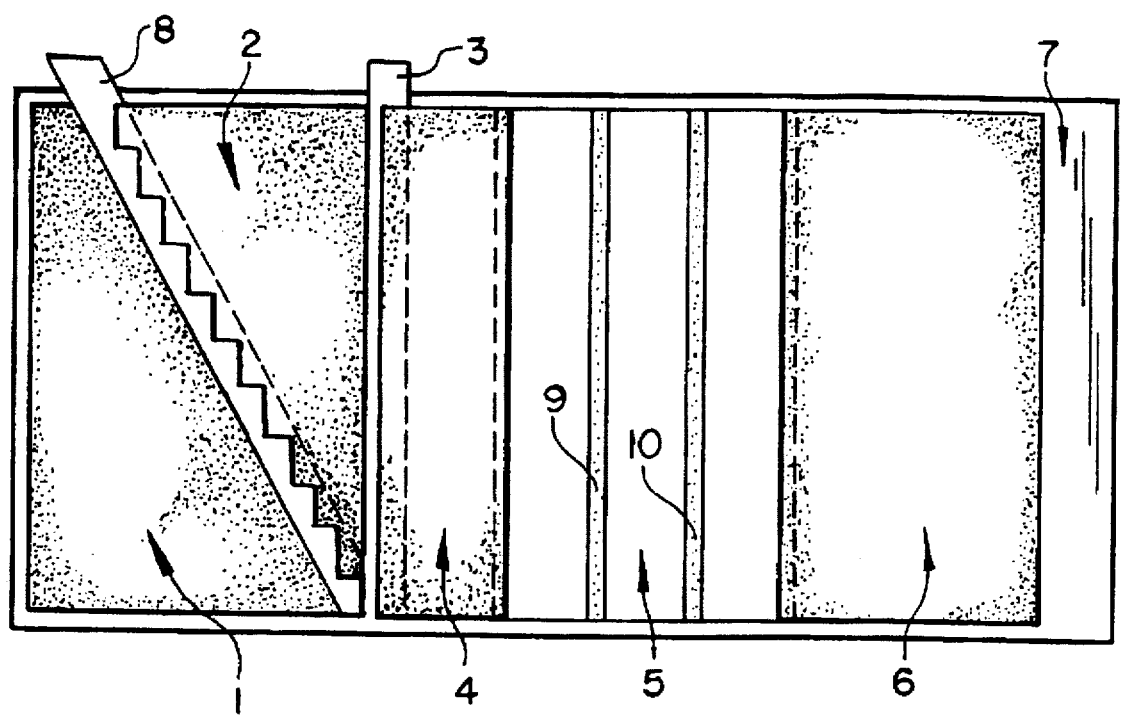
FIG. 8 is an illustration of an example of a gradient lateral flow device that could be used to establish a stepped analyte gradient.
Figure 9:
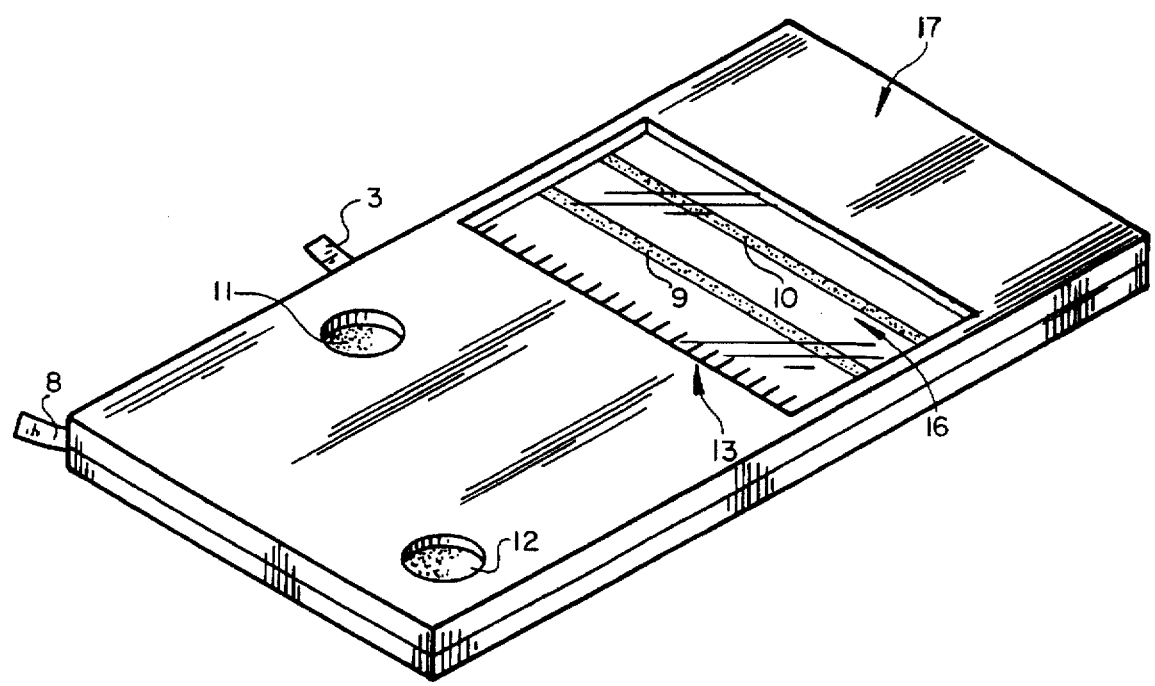
FIG. 9 is an illustration of an example of a gradient lateral flow device, showing the side and top housing.

In FIG. 8 there is shown a gradient lateral flow device wherein a stepped analyte gradient is established.

Figure 11:
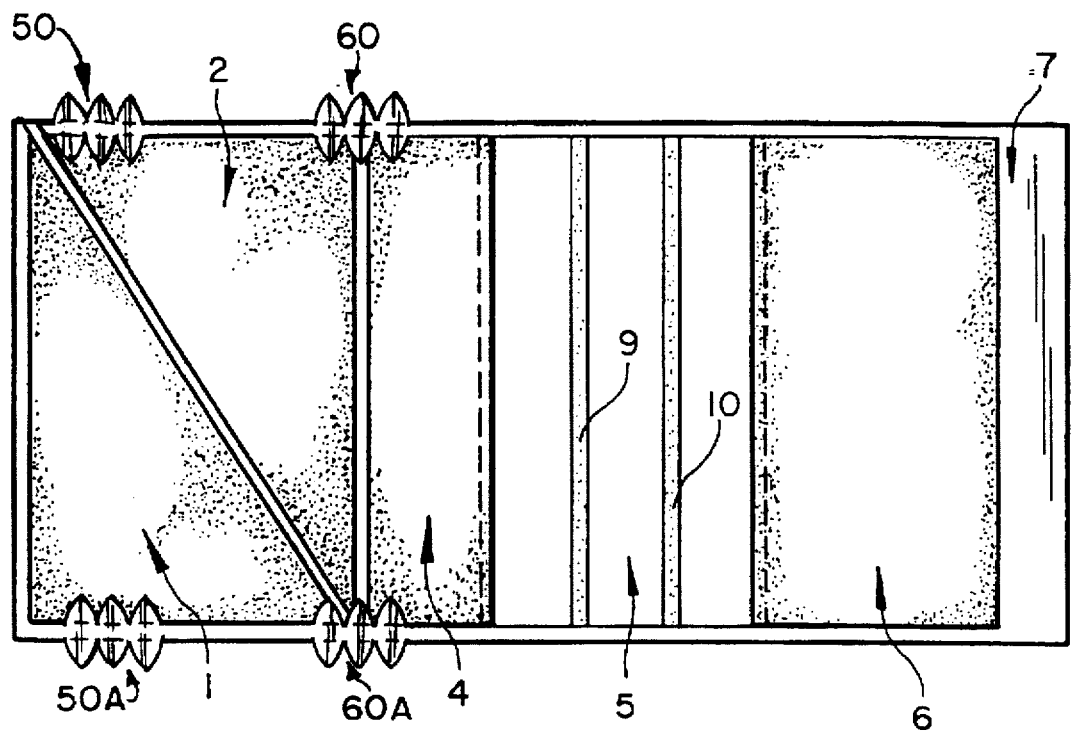
FIG. 11 is an illustration of an example of a gradient lateral flow device in which various pads are brought into contact by exerting pressure against the collapsable structures shown along each side.

In FIG. 11 there is shown a gradient lateral flow device in which the material to which the various pads are attached (7)

contains accordion-like ridges that will collapse under pressure. The ridges that separate the sample application pad (2) from the diluent application pad (1), i.e. ridges (50) and (50A) will be designed to collapse first. The ridges that separate the diluent application pad (1) from the indicator zone (4), i.e. ridges (60) and (60A) will be designed to collapse subsequently.

Other embodiments are within the following claims.

What is claimed is:

1. A method of determining the concentration of an analyte in a sample, said method comprising:
   (a) establishing an analyte gradient in a lateral flow device;
   (b) bringing said gradient into liquid contact with an indicator zone containing a mobile binding member conjugated to a signalling substance, wherein said mobile binding member either (i) binds to said analyte or (ii) competes with said analyte for binding to a fixed binding member contained in a test zone; and
   (c) bringing said indicator zone into liquid contact with said test zone containing said fixed binding member, wherein said fixed binding member binds to said analyte or said mobile binding member, and a detectable signal that indicates the concentration of said analyte is produced.

2. A method of determining the concentration of an analyte in a sample, said method comprising:
   (a) establishing an analyte gradient;
   (b) bringing said gradient into liquid contact with a test zone containing a fixed binding member wherein a detectable signal that indicates the concentration of said analyte is produced.

3. A method of determining the concentration of an analyte in a sample, said method comprising:
   (a) establishing an analyte gradient in a lateral flow device;
   (b) bringing said gradient into liquid contact with a test zone containing a fixed binding member wherein said fixed binding member binds to said analyte; and
   (c) bringing an indicator zone into liquid contact with said test zone, wherein (i) said indicator zone contains a mobile binding member conjugated to a signaling substance and (ii) said mobile binding member binds to said analyte or said fixed binding member contained in said test zone, and a detectable signal that indicates the concentration of said analyte is produced.

4. The method of claim 1, claim 2, or claim 3, wherein said analyte is an antibody, an antibody fragment, an enzyme, a hormone, a growth factor, a neurotransmitter, a nucleic acid, or a hapten.

5. The method of claim 1, claim 2, or claim 3, wherein said analyte is a bacterial, fungal, parasitic, or viral antigen.

6. The method of claim 1, claim 2,or claim 3, wherein said analyte is a drug which is a barbiturate, an amphetamine, methadone, morphine, cocaine, codeine, dilaudid, tetrahydrocannabinol, or diazepan.

7. The method of claim 1, claim 2, or claim 3, wherein said analyte is used in the manufacture of food, industrial agents, or chemical products.

8. The method of claim 1, claim 2, or claim 3, wherein said analyte is a bulking agent, a vitamin, a colorant, a flavorant, an insecticide, an herbicide, a fertilizer, a surfactant, an adhesive, a resin, an organic pollutant, a hapten, or a process chemical.

9. The method of claim 1, claim 2, or claim 3, wherein said sample is a biological fluid.

10. The method of claim 9, wherein said biological fluid is whole blood, serum, plasma, cerebrospinal fluid, or urine.

11. The method of claim 1, claim 2, or claim 3, wherein said sample is an environmental sample.

12. The method of claim 11, wherein said environmental sample is soil, foliage, or water.

13. The method of claim 1, claim 2, or claim 3, wherein said mobile binding member and said fixed binding member are selected from the group consisting of an antibody, an antibody fragment, a hapten, a cell, a cell fragment, a nucleic acid molecule, a cell surface receptor, a lectin, a carbohydrate, avidin, biotin, Protein A, or an enzyme.

14. The method of claim 1, claim 2, or claim 3, wherein said signalling substance comprises a liposome, a latex bead, colored silica, colloidal metal, a chemiluminescer, an enzyme, a fluorophore, or a chromophore.

15. The method of claim 2, wherein said analyte binds to said fixed binding member.

16. The method of claim 1, claim 2, or claim 3, wherein said analyte gradient is established by:
   (a) applying said sample to a defined sample application region comprising an absorbent material having a width which tapers from a large base to a small tip;
   (b) applying a diluent to a defined diluent application region comprising an absorbent material; and
   (c) bringing said sample application region into contact with said diluent application region to establish an analyte gradient front.

17. The method of claim 16, wherein said sample and diluent application pads have smooth edges.

18. The method of claim 16, wherein at least one of said sample and diluent application pads has at least one stepped edge.

19. A lateral flow device for determining the concentration of an analyte in a sample, said device comprising:
   (a) a defined sample application region comprising an absorbent material having a width which tapers from a large base to a small tip; and
   (b) a defined diluent application region comprising an absorbent material; wherein said regions are physically arranged to be brought into liquid contact with each other to establish an analyte gradient front; and
   (c) a test zone, physically arranged to be brought into liquid contact with said analyte gradient front, wherein said test zone contains a reagent for providing a detectable signal that indicates the concentration of said analyte.

20. The device of claim 19, wherein said reagent in said test zone is a fixed binding member which binds either to said analyte or a mobile binding member, said device further comprising an indicator zone containing said mobile binding member conjugated to a signalling substance, wherein said mobile binding member either (i) binds to said analyte or (ii) competes with said analyte for binding to a fixed binding member contained in said test zone.

21. The device of claim 20, wherein said indicator zone is positioned downstream from said sample and diluent application regions and upstream from said test zone.

22. The device of claim 20, wherein said indicator zone is positioned downstream from said sample application region and said diluent application region, such that the indicator zone can be brought into liquid contact with the test zone to effect reverse flow of the mobile binding member from the indicator zone across the test zone.

23. The device of claim 20, further comprising a control zone containing a second fixed binding member, wherein said second fixed binding member binds to said mobile binding member to produce a detectable signal that is independent of said analyte.

24. The device of claim 23, further comprising one or more absorbent pads that are positioned to facilitate the lateral flow of said analyte gradient front through the indicator zone, the test zone, or the control zone.

25. The device of claim 19, wherein said diluent application region also has a width which tapers from a large base to a small tip and wherein the tip of said sample application region is adjacent to the base of said diluent application region, and vice-versa.

26. The device of claim 19, wherein said sample application region and said diluent application region have smooth edges.

27. The device of claim 19, wherein at least one of said sample and diluent application regions has at least one stepped edge.

28. The device of claim 19, further comprising a physical barrier between said sample application region and said diluent application region, wherein said sample application region is brought into liquid contact with said diluent application region by dislocation of said physical barrier.

29. The device of claim 28, wherein said physical barrier is a strip of hydrophobic polystyrene.

30. The device of claim 19, wherein said sample application region is brought into liquid contact with said diluent application region by bringing a first surface, to which said sample application region is attached, into contact with a second surface, to which said diluent application region is attached.

31. The device of claim 30, wherein said first surface and said second surface are attached to one another along one edge, each of said surfaces having an opposite unattached edge, said contact being established by bringing said unattached edge of said first surface into contact with said unattached edge of said second surface.

32. The device of claim 30, wherein said first surface and said second surface are separated from each other by ridges which collapse and fold like an accordion under pressure and are brought into contact by applying pressure to one or more points on said device, said pressure being sufficient to collapse said ridges and thereby bring said first surface into contact with said second surface.

33. The device of claim 19, further comprising a drain whereby sample, diluent, or reagent used to detect said analyte can be removed from said device subsequent to traversal through said device.

34. The device of claim 19, further comprising reservoirs containing buffers or reagents used to detect said analyte, wherein said reservoirs are positioned adjacent to a point of application.

35. A kit comprising
 (a) the device of claim 19, and
 (b) one or more diluents.

36. A kit comprising:
 (a) the device of claim 19, and
 (b) one or more reagents.

37. A kit comprising:
 (a) the device of claim 19,
 (b) one or more diluents, and
 (c) one or more reagents.

* * * * *